United States Patent
Strausbaugh et al.

(10) Patent No.: US 11,432,850 B2
(45) Date of Patent: *Sep. 6, 2022

(54) POLYAXIAL BONE ANCHORS WITH INCREASED ANGULATION

(71) Applicant: DePuy Synthes Products, Inc., Raynham, MA (US)

(72) Inventors: William L. Strausbaugh, Myerstown, PA (US); Sean Saidha, Franklin, MA (US); Boyd A. Wolf, Roswell, GA (US)

(73) Assignee: DePuy Synthes Products, Inc., Raynham, MA (US)

( * ) Notice: Subject to any disclaimer, the term of this patent is extended or adjusted under 35 U.S.C. 154(b) by 3 days.

This patent is subject to a terminal disclaimer.

(21) Appl. No.: 16/790,999

(22) Filed: Feb. 14, 2020

(65) Prior Publication Data

US 2020/0179018 A1 Jun. 11, 2020

Related U.S. Application Data

(63) Continuation of application No. 15/803,088, filed on Nov. 3, 2017, now Pat. No. 10,595,908, which is a continuation of application No. 14/187,947, filed on Feb. 24, 2014, now Pat. No. 9,848,918, which is a continuation of application No. 13/688,600, filed on Nov. 29, 2012, now Pat. No. 9,504,498, which is a continuation of application No. 13/329,755, filed on Dec. 19, 2011, now Pat. No. 8,679,162, which is a (Continued)

(51) Int. Cl.
*A61B 17/70* (2006.01)

(52) U.S. Cl.
CPC ...... *A61B 17/7049* (2013.01); *A61B 17/7032* (2013.01); *A61B 17/7037* (2013.01); *A61B 17/7038* (2013.01)

(58) Field of Classification Search
CPC ............................................ A61B 17/70–7046
See application file for complete search history.

(56) References Cited

U.S. PATENT DOCUMENTS

| 405,546 A | 6/1889 | Frist |
|---|---|---|
| 513,630 A | 1/1894 | Beard |
| 527,678 A | 10/1894 | Francis |

(Continued)

FOREIGN PATENT DOCUMENTS

| CA | 2289629 A1 | 11/1998 |
|---|---|---|
| CN | 1997321 A | 7/2007 |

(Continued)

OTHER PUBLICATIONS

Aebi et al., "AO ASIF Principles in Spine Surgery", Springer, 1998, 186-190.

(Continued)

*Primary Examiner* — Eduardo C Robert
*Assistant Examiner* — Steven J Cotroneo
(74) *Attorney, Agent, or Firm* — BakerHostetler

(57) ABSTRACT

A polyaxial bone anchor has a locking element shaped and configured to allow an anchoring member (e.g., a screw or hook) to polyaxially rotate at large angles about a central axis of the bone anchor before compression locking the anchoring member within an anchor head.

22 Claims, 6 Drawing Sheets

Related U.S. Application Data continuation of application No. 11/603,428, filed on Nov. 21, 2006, now Pat. No. 8,100,946.

(60) Provisional application No. 60/739,100, filed on Nov. 21, 2005.

(56) References Cited

U.S. PATENT DOCUMENTS

| | | |
|---|---|---|
| 802,896 A | 10/1905 | Webb |
| 2,005,348 A | 6/1935 | Michell |
| 2,338,659 A | 1/1944 | Morehouse |
| 2,396,925 A | 3/1946 | Morehouse |
| 3,173,987 A | 3/1965 | Potruch |
| 3,463,427 A | 8/1969 | Fisher |
| 4,447,934 A | 5/1984 | Anscher |
| 4,601,491 A | 7/1986 | Bell et al. |
| 4,719,905 A | 1/1988 | Steffee |
| 4,805,602 A | 2/1989 | Puno et al. |
| 4,846,614 A | 7/1989 | Steinbock |
| 4,863,383 A | 9/1989 | Grafelmann |
| 4,936,851 A | 6/1990 | Fox et al. |
| 4,944,475 A | 7/1990 | Ono et al. |
| 4,946,458 A | 8/1990 | Harms et al. |
| 5,005,562 A | 4/1991 | Cotrel |
| 5,116,337 A | 5/1992 | Johnson |
| 5,129,388 A | 7/1992 | Vignaud et al. |
| 5,207,678 A | 5/1993 | Harms et al. |
| 5,242,446 A | 9/1993 | Steffee et al. |
| 5,270,678 A | 12/1993 | Gambut et al. |
| 5,282,825 A | 2/1994 | Muck et al. |
| 5,304,178 A | 4/1994 | Stahurski |
| 5,306,275 A | 4/1994 | Bryan |
| 5,306,285 A | 4/1994 | Miller et al. |
| 5,312,410 A | 5/1994 | Miller et al. |
| 5,360,431 A | 11/1994 | Puno et al. |
| 5,383,882 A | 1/1995 | Buess et al. |
| 5,395,374 A | 3/1995 | Miller et al. |
| 5,413,576 A | 5/1995 | Rivard |
| 5,413,602 A | 5/1995 | Metz-Stavenhagen |
| 5,417,684 A | 5/1995 | Jackson et al. |
| 5,443,467 A | 8/1995 | Biedermann et al. |
| 5,449,361 A | 9/1995 | Preissman |
| 5,466,237 A | 11/1995 | Byrd et al. |
| 5,468,241 A | 11/1995 | Metz-Stavenhagen et al. |
| 5,474,555 A | 12/1995 | Puno et al. |
| 5,476,464 A | 12/1995 | Metz-Stavenhagen et al. |
| 5,486,174 A | 1/1996 | Fournet-Fayard et al. |
| 5,496,321 A | 3/1996 | Puno et al. |
| 5,498,262 A | 3/1996 | Bryan |
| 5,501,684 A | 3/1996 | Schlapfer et al. |
| 5,520,689 A | 5/1996 | Schlaepfer et al. |
| 5,520,690 A | 5/1996 | Errico et al. |
| 5,527,183 A | 6/1996 | O'Brien |
| 5,531,746 A | 7/1996 | Errico et al. |
| 5,534,001 A | 7/1996 | Schlapfer et al. |
| 5,536,268 A | 7/1996 | Griss |
| 5,536,270 A | 7/1996 | Songer et al. |
| 5,540,698 A | 7/1996 | Preissman |
| 5,549,608 A | 8/1996 | Errico et al. |
| 5,549,677 A | 8/1996 | Duerr et al. |
| 5,554,157 A | 9/1996 | Errico et al. |
| 5,562,661 A | 10/1996 | Yoshimi et al. |
| 5,575,792 A | 11/1996 | Errico et al. |
| 5,578,033 A | 11/1996 | Errico et al. |
| 5,584,832 A | 12/1996 | Schlaepfer |
| 5,584,834 A | 12/1996 | Errico et al. |
| 5,586,984 A | 12/1996 | Errico et al. |
| 5,601,261 A | 2/1997 | Koike |
| 5,601,429 A | 2/1997 | Blacklock |
| 5,605,457 A | 2/1997 | Bailey et al. |
| 5,605,458 A | 2/1997 | Bailey et al. |
| 5,607,304 A | 3/1997 | Bailey et al. |
| 5,607,426 A | 3/1997 | Ralph et al. |
| 5,609,593 A | 3/1997 | Errico et al. |
| 5,609,594 A | 3/1997 | Errico et al. |
| 5,624,442 A | 4/1997 | Mellinger et al. |
| 5,643,260 A | 7/1997 | Doherty |
| 5,643,262 A | 7/1997 | Metz-Stavenhagen et al. |
| 5,643,265 A | 7/1997 | Errico et al. |
| 5,645,544 A | 7/1997 | Tai et al. |
| 5,647,873 A * | 7/1997 | Errico ............... A61F 2/30721 606/264 |
| 5,662,651 A | 9/1997 | Tornier et al. |
| 5,667,508 A | 9/1997 | Errico et al. |
| 5,669,911 A | 9/1997 | Errico et al. |
| 5,672,175 A | 9/1997 | Martin |
| 5,683,390 A | 11/1997 | Metz-Stavenhagen et al. |
| 5,683,392 A | 11/1997 | Richelsoph et al. |
| 5,683,404 A | 11/1997 | Johnson |
| 5,688,273 A | 11/1997 | Errico et al. |
| 5,690,630 A | 11/1997 | Errico et al. |
| 5,694,760 A | 12/1997 | Baxter |
| 5,704,939 A | 1/1998 | Justin |
| 5,725,582 A | 3/1998 | Bevan et al. |
| 5,725,588 A | 3/1998 | Errico et al. |
| 5,728,098 A | 3/1998 | Sherman et al. |
| 5,733,285 A | 3/1998 | Errico et al. |
| 5,738,685 A | 4/1998 | Halm et al. |
| 5,772,663 A | 6/1998 | Whiteside et al. |
| 5,782,831 A | 7/1998 | Sherman et al. |
| 5,782,833 A | 7/1998 | Haider |
| 5,797,911 A | 8/1998 | Sherman et al. |
| 5,810,818 A | 9/1998 | Errico et al. |
| 5,817,094 A | 10/1998 | Errico et al. |
| 5,860,987 A | 1/1999 | Ratcliff et al. |
| 5,863,293 A | 1/1999 | Richelsoph |
| 5,868,748 A | 2/1999 | Burke |
| 5,876,402 A | 3/1999 | Errico et al. |
| 5,879,350 A | 3/1999 | Sherman et al. |
| 5,882,350 A | 3/1999 | Ralph et al. |
| 5,885,286 A | 3/1999 | Sherman et al. |
| 5,888,204 A | 3/1999 | Ralph et al. |
| 5,891,145 A | 4/1999 | Morrison et al. |
| 5,899,940 A | 5/1999 | Carchidi et al. |
| 5,902,305 A | 5/1999 | Beger et al. |
| 5,938,663 A | 8/1999 | Petreto |
| 5,951,287 A | 9/1999 | Hawkinson |
| 5,961,329 A | 10/1999 | Stucki-McCormick |
| 5,964,760 A | 10/1999 | Richelsoph |
| 6,001,098 A | 12/1999 | Metz-Stavenhagen et al. |
| 6,010,503 A | 1/2000 | Richelsoph et al. |
| 6,015,409 A | 1/2000 | Jackson |
| 6,017,177 A | 1/2000 | Lanham |
| 6,019,760 A | 2/2000 | Metz-Stavenhagen et al. |
| 6,022,350 A | 2/2000 | Ganem |
| 6,053,917 A | 4/2000 | Sherman et al. |
| 6,063,090 A | 5/2000 | Schlaepfer |
| 6,074,391 A | 6/2000 | Metz-Stavenhagen et al. |
| 6,077,262 A | 6/2000 | Schlaepfer et al. |
| 6,077,263 A | 6/2000 | Ameil et al. |
| 6,083,224 A | 7/2000 | Gertzbein et al. |
| 6,090,110 A | 7/2000 | Metz-Stavenhagen |
| 6,126,662 A | 10/2000 | Carmichael et al. |
| 6,132,432 A | 10/2000 | Richelsoph |
| 6,183,472 B1 | 2/2001 | Lutz |
| 6,214,006 B1 | 4/2001 | Metz-Stavenhagen |
| 6,217,331 B1 | 4/2001 | Rogers et al. |
| 6,224,598 B1 | 5/2001 | Jackson |
| 6,248,105 B1 | 6/2001 | Schlaepfer et al. |
| 6,261,287 B1 | 7/2001 | Metz-Stavenhagen |
| 6,273,914 B1 | 8/2001 | Papas |
| 6,280,442 B1 | 8/2001 | Barker et al. |
| 6,296,642 B1 | 10/2001 | Morrison et al. |
| 6,325,802 B1 | 12/2001 | Frigg |
| 6,355,040 B1 * | 3/2002 | Richelsoph ........ A61B 17/7032 606/272 |
| 6,361,535 B2 | 3/2002 | Jackson |
| RE37,665 E | 4/2002 | Ralph et al. |
| 6,368,321 B1 | 4/2002 | Jackson |
| 6,402,752 B2 | 6/2002 | Schaeffler-Wachter et al. |
| 6,440,132 B1 | 8/2002 | Jackson |
| 6,443,953 B1 | 9/2002 | Perra et al. |
| 6,443,955 B1 | 9/2002 | Ahrend et al. |
| 6,451,021 B1 | 9/2002 | Ralph et al. |

(56) References Cited

U.S. PATENT DOCUMENTS

| | | |
|---|---|---|
| 6,454,768 B1 | 9/2002 | Jackson |
| 6,454,772 B1 | 9/2002 | Jackson |
| 6,471,705 B1 | 10/2002 | Biedermann et al. |
| 6,482,207 B1 | 11/2002 | Errico |
| 6,485,491 B1 | 11/2002 | Farris et al. |
| 6,491,696 B1 | 12/2002 | Kunkel |
| 6,508,820 B2 | 1/2003 | Bales |
| 6,514,255 B1 | 2/2003 | Ferree |
| 6,520,963 B1 | 2/2003 | McKinley |
| 6,533,226 B2 | 3/2003 | Geiger |
| 6,537,070 B1 | 3/2003 | Stucki-McCormick |
| 6,537,276 B2 | 3/2003 | Metz-Stavenhagen |
| 6,554,831 B1 | 4/2003 | Rivard et al. |
| 6,558,387 B2 | 5/2003 | Errico et al. |
| 6,565,565 B1 | 5/2003 | Yuan et al. |
| 6,585,740 B2 | 7/2003 | Schlapfer et al. |
| 6,616,667 B1 | 9/2003 | Steiger et al. |
| 6,626,908 B2 | 9/2003 | Cooper et al. |
| 6,641,586 B2 | 11/2003 | Varieur |
| 6,641,588 B2 | 11/2003 | Citron et al. |
| 6,660,004 B2 | 12/2003 | Barker et al. |
| 6,689,140 B2 | 2/2004 | Cohen |
| 6,695,852 B2 | 2/2004 | Gleason |
| 6,716,214 B1 | 4/2004 | Jackson |
| 6,726,687 B2 | 4/2004 | Jackson |
| 6,736,820 B2 | 5/2004 | Biedermann et al. |
| 6,738,527 B2 | 5/2004 | Kuwata et al. |
| 6,740,086 B2 | 5/2004 | Richelsoph |
| 6,749,613 B1 | 6/2004 | Conchy et al. |
| 6,755,829 B1 | 6/2004 | Bono et al. |
| 6,770,075 B2 | 8/2004 | Howland |
| 6,780,186 B2 | 8/2004 | Errico et al. |
| 6,783,527 B2 | 8/2004 | Drewry et al. |
| 6,802,844 B2 | 10/2004 | Ferree |
| 6,827,719 B2 | 12/2004 | Ralph et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,866,664 B2 | 3/2005 | Schaer et al. |
| 6,869,433 B2 * | 3/2005 | Glascott ............. A61B 17/7037 606/308 |
| 6,887,275 B2 | 5/2005 | Carchidi et al. |
| 6,918,911 B2 * | 7/2005 | Biedermann ...... A61B 17/7037 606/267 |
| 6,933,440 B2 | 8/2005 | Ichikawa et al. |
| 6,964,666 B2 | 11/2005 | Jackson |
| 6,974,460 B2 | 12/2005 | Carbone et al. |
| 6,981,973 B2 | 1/2006 | McKinley |
| 7,008,227 B2 | 3/2006 | Carmichael et al. |
| 7,018,378 B2 | 3/2006 | Biedermann et al. |
| RE39,089 E | 5/2006 | Ralph et al. |
| 7,073,415 B2 | 7/2006 | Casutt et al. |
| 7,081,117 B2 | 7/2006 | Bono et al. |
| 7,087,057 B2 | 8/2006 | Konieczynski et al. |
| D527,678 S | 9/2006 | Warner |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,131,467 B2 | 11/2006 | Gao et al. |
| 7,144,396 B2 | 12/2006 | Shluzas |
| 7,163,539 B2 | 1/2007 | Abdelgany et al. |
| 7,175,622 B2 | 2/2007 | Farris |
| 7,186,255 B2 | 3/2007 | Baynham et al. |
| 7,211,086 B2 | 5/2007 | Biedermann et al. |
| 7,223,268 B2 | 5/2007 | Biedermann |
| 7,250,052 B2 | 7/2007 | Landry et al. |
| 7,270,665 B2 | 9/2007 | Morrison et al. |
| 7,316,684 B1 | 1/2008 | Baccelli et al. |
| 7,322,548 B2 | 1/2008 | Mielke et al. |
| 7,330,490 B2 | 2/2008 | Furukawa et al. |
| 7,338,490 B2 | 3/2008 | Ogilvie et al. |
| 7,445,627 B2 * | 11/2008 | Hawkes ............. A61B 17/7032 606/269 |
| 7,452,360 B2 | 11/2008 | Trudeau et al. |
| 7,476,239 B2 * | 1/2009 | Jackson ............. A61B 17/7037 606/266 |
| 7,547,319 B2 | 6/2009 | Segal et al. |
| 7,591,839 B2 | 9/2009 | Biedermann et al. |
| 7,592,546 B2 | 9/2009 | Johansson |
| 7,645,282 B2 | 1/2010 | Huxel et al. |
| 7,648,520 B2 | 1/2010 | Markworth |
| 7,691,131 B2 | 4/2010 | Graf |
| 7,708,762 B2 | 5/2010 | McCarthy et al. |
| 7,766,944 B2 | 8/2010 | Metz-Stavenhagen |
| 7,780,706 B2 | 8/2010 | Marino et al. |
| 7,785,352 B2 | 8/2010 | Snyder et al. |
| 7,785,354 B2 | 8/2010 | Biedermann et al. |
| 7,799,054 B2 | 9/2010 | Kwak et al. |
| 7,803,174 B2 | 9/2010 | Denis et al. |
| 7,806,895 B2 | 10/2010 | Weier et al. |
| 7,819,902 B2 | 10/2010 | Abdelgany et al. |
| 7,951,172 B2 | 5/2011 | Chao et al. |
| 7,967,849 B2 | 6/2011 | Carson et al. |
| 8,001,946 B2 | 8/2011 | Leitl |
| 8,002,806 B2 | 8/2011 | Justis |
| 8,029,513 B2 | 10/2011 | Konno et al. |
| 8,029,546 B2 | 10/2011 | Capote et al. |
| 8,038,701 B2 | 10/2011 | Rock et al. |
| 8,096,998 B2 | 1/2012 | Cresina |
| 8,100,946 B2 | 1/2012 | Strausbaugh et al. |
| 8,137,356 B2 | 3/2012 | Hestad et al. |
| 8,162,946 B2 | 4/2012 | Baccelli et al. |
| 8,162,986 B2 | 4/2012 | Zehnder |
| 8,172,772 B2 | 5/2012 | Zwolinski et al. |
| 8,197,517 B1 | 6/2012 | Lab et al. |
| 8,216,245 B2 | 7/2012 | Gil et al. |
| 8,221,464 B2 | 7/2012 | Belliard et al. |
| 8,231,626 B2 | 7/2012 | Hulliger et al. |
| 8,241,333 B2 | 8/2012 | Jackson |
| 8,246,659 B2 | 8/2012 | Vonwiller et al. |
| 8,257,367 B2 | 9/2012 | Bryant et al. |
| 8,308,782 B2 | 11/2012 | Jackson |
| 8,317,836 B2 | 11/2012 | Zuckerman et al. |
| 8,323,318 B2 | 12/2012 | Baccelli et al. |
| 8,444,681 B2 | 5/2013 | Jackson et al. |
| 8,469,960 B2 | 6/2013 | Hutton et al. |
| 8,469,966 B2 | 6/2013 | Allen et al. |
| 8,556,938 B2 | 10/2013 | Jackson et al. |
| 8,628,558 B2 | 1/2014 | Harvey et al. |
| 8,632,572 B2 | 1/2014 | Darst et al. |
| 8,663,298 B2 | 3/2014 | Keyer et al. |
| 8,758,411 B1 | 6/2014 | Rayon et al. |
| 8,814,910 B2 | 8/2014 | Baccelli et al. |
| 8,840,652 B2 | 9/2014 | Jackson |
| 8,870,869 B2 | 10/2014 | Meunier et al. |
| 8,870,870 B2 | 10/2014 | Baccelli et al. |
| 8,882,803 B2 | 11/2014 | Iott et al. |
| 8,911,470 B2 | 12/2014 | Mirza et al. |
| 8,911,478 B2 | 12/2014 | Jackson et al. |
| 8,911,479 B2 | 12/2014 | Jackson et al. |
| 8,926,672 B2 | 1/2015 | Jackson et al. |
| 8,979,904 B2 | 3/2015 | Jackson et al. |
| 8,998,959 B2 | 4/2015 | Jackson et al. |
| 8,998,961 B1 | 4/2015 | Ziemek et al. |
| 9,039,708 B2 | 5/2015 | Larroque-Lahitette |
| 9,168,069 B2 | 10/2015 | Jackson et al. |
| 9,216,041 B2 | 12/2015 | Jackson et al. |
| 9,320,546 B2 | 4/2016 | Keyer et al. |
| 9,326,796 B2 | 5/2016 | Harvey et al. |
| 9,393,047 B2 | 7/2016 | Jackson et al. |
| 9,439,681 B2 | 9/2016 | Keyer et al. |
| 9,451,993 B2 | 9/2016 | Jackson et al. |
| 9,480,517 B2 | 11/2016 | Jackson et al. |
| 9,504,496 B2 | 11/2016 | Jackson et al. |
| 9,522,021 B2 | 12/2016 | Jackson et al. |
| 9,636,146 B2 | 5/2017 | Jackson et al. |
| 9,717,533 B2 | 8/2017 | Jackson et al. |
| 9,717,534 B2 | 8/2017 | Jackson et al. |
| 10,105,163 B2 | 10/2018 | Keyer et al. |
| 10,136,923 B2 | 11/2018 | Keyer et al. |
| 10,154,859 B2 | 12/2018 | Keyer et al. |
| 10,405,892 B2 | 9/2019 | Harvey et al. |
| 10,595,908 B2 * | 3/2020 | Strausbaugh ...... A61B 17/7037 |

(56) References Cited

U.S. PATENT DOCUMENTS

| | | |
|---|---|---|
| 2001/0047173 A1 | 11/2001 | Schlapfer et al. |
| 2002/0045899 A1 | 4/2002 | Errico et al. |
| 2002/0068940 A1 | 6/2002 | Gaines |
| 2002/0069537 A1 | 6/2002 | Wenzler |
| 2002/0103487 A1 | 8/2002 | Errico et al. |
| 2002/0117321 A1 | 8/2002 | Beebe et al. |
| 2002/0120272 A1 | 8/2002 | Yuan et al. |
| 2002/0133154 A1 | 9/2002 | Saint Martin |
| 2002/0138077 A1 | 9/2002 | Ferree |
| 2002/0143341 A1 | 10/2002 | Biedermann et al. |
| 2002/0151900 A1 | 10/2002 | Glascott |
| 2003/0100896 A1 | 5/2003 | Biedermann et al. |
| 2003/0100904 A1 | 5/2003 | Biedermann |
| 2003/0125741 A1* | 7/2003 | Biedermann ...... A61B 17/7032 606/278 |
| 2003/0125742 A1 | 7/2003 | Yuan et al. |
| 2003/0149431 A1 | 8/2003 | Varieur |
| 2003/0153912 A1* | 8/2003 | Graf ................ A61B 17/7058 606/256 |
| 2003/0163133 A1 | 8/2003 | Altarac et al. |
| 2003/0176861 A1 | 9/2003 | Reed |
| 2004/0006342 A1 | 1/2004 | Altarac et al. |
| 2004/0024464 A1 | 2/2004 | Errico et al. |
| 2004/0039384 A1 | 2/2004 | Boehm et al. |
| 2004/0111088 A1 | 6/2004 | Picetti et al. |
| 2004/0138660 A1 | 7/2004 | Serhan |
| 2004/0138662 A1 | 7/2004 | Landry et al. |
| 2004/0143265 A1 | 7/2004 | Landry et al. |
| 2004/0153077 A1 | 8/2004 | Biedermann et al. |
| 2004/0157186 A1 | 8/2004 | Abels et al. |
| 2004/0162558 A1 | 8/2004 | Hegde et al. |
| 2004/0172022 A1 | 9/2004 | Landry et al. |
| 2004/0181224 A1 | 9/2004 | Biedermann et al. |
| 2004/0186473 A1 | 9/2004 | Cournoyer et al. |
| 2004/0186474 A1 | 9/2004 | Matthis et al. |
| 2004/0193160 A1 | 9/2004 | Richelsoph |
| 2004/0199169 A1 | 10/2004 | Koons et al. |
| 2004/0225292 A1 | 11/2004 | Sasso et al. |
| 2004/0230192 A1 | 11/2004 | Graf |
| 2004/0236330 A1 | 11/2004 | Purcell et al. |
| 2004/0249378 A1 | 12/2004 | Saint et al. |
| 2004/0249380 A1 | 12/2004 | Glascott |
| 2004/0267264 A1 | 12/2004 | Konieczynski et al. |
| 2005/0033298 A1 | 2/2005 | Hawkes et al. |
| 2005/0049588 A1 | 3/2005 | Jackson |
| 2005/0049589 A1 | 3/2005 | Jackson |
| 2005/0055026 A1 | 3/2005 | Biedermann et al. |
| 2005/0080415 A1 | 4/2005 | Keyer et al. |
| 2005/0080420 A1 | 4/2005 | Farris et al. |
| 2005/0143737 A1 | 6/2005 | Pafford et al. |
| 2005/0154389 A1 | 7/2005 | Selover et al. |
| 2005/0154391 A1* | 7/2005 | Doherty ............ A61B 17/7037 606/278 |
| 2005/0171537 A1 | 8/2005 | Mazel et al. |
| 2005/0171542 A1 | 8/2005 | Biedermann et al. |
| 2005/0177154 A1 | 8/2005 | Moumene et al. |
| 2005/0177166 A1 | 8/2005 | Timm et al. |
| 2005/0177179 A1 | 8/2005 | Baynham et al. |
| 2005/0187548 A1* | 8/2005 | Butler ................ A61B 17/7038 606/278 |
| 2005/0192571 A1 | 9/2005 | Abdelgany |
| 2005/0203515 A1 | 9/2005 | Doherty et al. |
| 2005/0203516 A1* | 9/2005 | Biedermann ........ A61B 17/701 606/267 |
| 2005/0209592 A1 | 9/2005 | Schlapfer et al. |
| 2005/0216001 A1 | 9/2005 | David |
| 2005/0216003 A1* | 9/2005 | Biedermann ...... A61B 17/7032 606/279 |
| 2005/0228378 A1 | 10/2005 | Kalfas et al. |
| 2005/0228385 A1 | 10/2005 | Iott et al. |
| 2005/0234421 A1 | 10/2005 | Mishima et al. |
| 2005/0234451 A1 | 10/2005 | Markworth |
| 2005/0261687 A1 | 11/2005 | Garamszegi et al. |
| 2005/0277928 A1 | 12/2005 | Boschert |
| 2005/0283157 A1* | 12/2005 | Coates ............... A61B 17/7037 606/268 |
| 2005/0288671 A1 | 12/2005 | Yuan et al. |
| 2006/0004357 A1 | 1/2006 | Lee et al. |
| 2006/0025767 A1 | 2/2006 | Khalili |
| 2006/0025770 A1 | 2/2006 | Schlapfer et al. |
| 2006/0036252 A1 | 2/2006 | Baynham et al. |
| 2006/0052818 A1 | 3/2006 | Drake et al. |
| 2006/0064091 A1 | 3/2006 | Ludwig et al. |
| 2006/0079892 A1 | 4/2006 | Roychowdhury et al. |
| 2006/0084993 A1 | 4/2006 | Landry et al. |
| 2006/0084995 A1 | 4/2006 | Biedermann et al. |
| 2006/0084996 A1 | 4/2006 | Metz-Stavenhagen |
| 2006/0089634 A1 | 4/2006 | Anderson et al. |
| 2006/0089643 A1 | 4/2006 | Mujwid |
| 2006/0100622 A1* | 5/2006 | Jackson ............. A61B 17/7037 606/304 |
| 2006/0106383 A1 | 5/2006 | Biedermann et al. |
| 2006/0111779 A1 | 5/2006 | Petersen |
| 2006/0129149 A1 | 6/2006 | Iott et al. |
| 2006/0142761 A1 | 6/2006 | Landry et al. |
| 2006/0149232 A1 | 7/2006 | Sasing |
| 2006/0149233 A1 | 7/2006 | Richelsoph |
| 2006/0149241 A1 | 7/2006 | Richelsoph et al. |
| 2006/0149244 A1* | 7/2006 | Amrein ............. A61B 17/7037 606/264 |
| 2006/0149265 A1 | 7/2006 | James et al. |
| 2006/0155277 A1 | 7/2006 | Metz-Stavenhagen |
| 2006/0173456 A1 | 8/2006 | Hawkes et al. |
| 2006/0200131 A1 | 9/2006 | Chao et al. |
| 2006/0212034 A1 | 9/2006 | Triplett et al. |
| 2006/0217717 A1 | 9/2006 | Whipple |
| 2006/0229611 A1 | 10/2006 | Avery et al. |
| 2006/0235385 A1 | 10/2006 | Whipple |
| 2006/0235393 A1 | 10/2006 | Bono et al. |
| 2006/0241594 A1 | 10/2006 | McCarthy et al. |
| 2006/0241599 A1 | 10/2006 | Konieczynski et al. |
| 2006/0241624 A1 | 10/2006 | Kizuka et al. |
| 2006/0247636 A1 | 11/2006 | Yuan et al. |
| 2006/0247668 A1 | 11/2006 | Park |
| 2006/0271047 A1 | 11/2006 | Jackson |
| 2006/0282080 A1 | 12/2006 | Todd et al. |
| 2006/0293659 A1* | 12/2006 | Alvarez ............. A61B 17/7037 606/305 |
| 2006/0293664 A1 | 12/2006 | Schumacher |
| 2007/0016200 A1 | 1/2007 | Jackson |
| 2007/0043365 A1 | 2/2007 | Ritland |
| 2007/0049932 A1 | 3/2007 | Richelsoph et al. |
| 2007/0055240 A1 | 3/2007 | Matthis et al. |
| 2007/0088357 A1 | 4/2007 | Johnson et al. |
| 2007/0090238 A1 | 4/2007 | Justis |
| 2007/0118118 A1 | 5/2007 | Kwak et al. |
| 2007/0118121 A1 | 5/2007 | Purcell et al. |
| 2007/0118123 A1 | 5/2007 | Strausbaugh et al. |
| 2007/0123860 A1 | 5/2007 | Francis et al. |
| 2007/0123870 A1 | 5/2007 | Jeon et al. |
| 2007/0135817 A1 | 6/2007 | Ensign |
| 2007/0161987 A1 | 7/2007 | Capote et al. |
| 2007/0161994 A1 | 7/2007 | Lowery et al. |
| 2007/0167946 A1 | 7/2007 | Triplett et al. |
| 2007/0167949 A1 | 7/2007 | Altarac et al. |
| 2007/0179501 A1 | 8/2007 | Firkins |
| 2007/0191844 A1 | 8/2007 | Carls et al. |
| 2007/0198014 A1 | 8/2007 | Graf et al. |
| 2007/0225711 A1 | 9/2007 | Ensign |
| 2007/0233087 A1 | 10/2007 | Schlapfer |
| 2007/0233091 A1 | 10/2007 | Naifeh et al. |
| 2007/0246614 A1 | 10/2007 | Allmann et al. |
| 2007/0250061 A1 | 10/2007 | Chin et al. |
| 2007/0250064 A1 | 10/2007 | Darois et al. |
| 2007/0270805 A1 | 11/2007 | Miller et al. |
| 2007/0270817 A1 | 11/2007 | Rezach |
| 2007/0270820 A1 | 11/2007 | Dickinson et al. |
| 2007/0270880 A1 | 11/2007 | Lindemann et al. |
| 2007/0282339 A1 | 12/2007 | Schwab |
| 2007/0288004 A1 | 12/2007 | Alvarez |
| 2008/0021455 A1 | 1/2008 | Chao et al. |
| 2008/0021456 A1 | 1/2008 | Gupta et al. |
| 2008/0039843 A1 | 2/2008 | Abdou |

(56) References Cited

U.S. PATENT DOCUMENTS

| | | |
|---|---|---|
| 2008/0058805 A1 | 3/2008 | Stuart |
| 2008/0058812 A1 | 3/2008 | Zehnder |
| 2008/0086126 A1 | 4/2008 | Miller |
| 2008/0103502 A1 | 5/2008 | Capote et al. |
| 2008/0140075 A1 | 6/2008 | Ensign et al. |
| 2008/0140135 A1 | 6/2008 | Konieczynski et al. |
| 2008/0154277 A1 | 6/2008 | Machalk et al. |
| 2008/0154308 A1 | 6/2008 | Sherman et al. |
| 2008/0177260 A1 | 7/2008 | McKinley et al. |
| 2008/0177323 A1 | 7/2008 | Null et al. |
| 2008/0188260 A1 | 8/2008 | Xiao et al. |
| 2008/0208257 A1 | 8/2008 | Matthys |
| 2008/0215095 A1 | 9/2008 | Biedermann et al. |
| 2008/0234743 A1 | 9/2008 | Marik |
| 2008/0243185 A1 | 10/2008 | Felix et al. |
| 2008/0249570 A1 | 10/2008 | Carson et al. |
| 2008/0262552 A1 | 10/2008 | Kim |
| 2008/0262553 A1 | 10/2008 | Hawkins et al. |
| 2008/0269810 A1 | 10/2008 | Zhang et al. |
| 2008/0294194 A1 | 11/2008 | Capote et al. |
| 2008/0294202 A1 | 11/2008 | Peterson et al. |
| 2008/0306553 A1 | 12/2008 | Zucherman et al. |
| 2008/0312692 A1 | 12/2008 | Brennan et al. |
| 2009/0088803 A1 | 4/2009 | Justis et al. |
| 2009/0093847 A1 | 4/2009 | Wilcox |
| 2009/0105770 A1 | 4/2009 | Berrevoets et al. |
| 2009/0149887 A1 | 6/2009 | Schlaepfer et al. |
| 2009/0187217 A1 | 7/2009 | Weiman et al. |
| 2009/0198280 A1 | 8/2009 | Spratt et al. |
| 2009/0259256 A1 | 10/2009 | Miller |
| 2009/0270916 A1 | 10/2009 | Ramsay et al. |
| 2010/0004694 A1 | 1/2010 | Little |
| 2010/0042165 A1 | 2/2010 | Aflatoon |
| 2010/0057125 A1 | 3/2010 | Viker |
| 2010/0087864 A1 | 4/2010 | Klein et al. |
| 2010/0094345 A1 | 4/2010 | Saidha et al. |
| 2010/0145394 A1 | 6/2010 | Harvey et al. |
| 2010/0168797 A1 | 7/2010 | Graf |
| 2010/0191286 A1 | 7/2010 | Butler |
| 2010/0198272 A1 | 8/2010 | Keyer et al. |
| 2010/0241172 A1 | 9/2010 | Biyani et al. |
| 2010/0249843 A1 | 9/2010 | Wegrzyn, III |
| 2010/0276051 A1 | 11/2010 | Kanehira |
| 2010/0292736 A1 | 11/2010 | Schwab |
| 2010/0298890 A1 | 11/2010 | Marino |
| 2010/0305621 A1 | 12/2010 | Wang et al. |
| 2010/0313428 A1 | 12/2010 | Mocanu |
| 2010/0318131 A1 | 12/2010 | James et al. |
| 2010/0324599 A1 | 12/2010 | Montello et al. |
| 2011/0087289 A1 | 4/2011 | Pham et al. |
| 2011/0106166 A1 | 5/2011 | Keyer et al. |
| 2011/0118791 A1 | 5/2011 | Nunley et al. |
| 2011/0213424 A1 | 9/2011 | Biedermann et al. |
| 2011/0230917 A1 | 9/2011 | Carson et al. |
| 2011/0270325 A1 | 11/2011 | Keyer et al. |
| 2011/0276051 A1 | 11/2011 | Blakemore et al. |
| 2012/0010629 A1 | 1/2012 | Mire et al. |
| 2012/0089194 A1 | 4/2012 | Strausbaugh et al. |
| 2012/0101533 A1 | 4/2012 | Purcell et al. |
| 2012/0109200 A1 | 5/2012 | Cahill et al. |
| 2012/0265249 A1 | 10/2012 | Fielding et al. |
| 2013/0012955 A1 | 1/2013 | Lin |
| 2013/0012995 A1 | 1/2013 | Butterfield et al. |
| 2013/0018421 A1 | 1/2013 | George et al. |
| 2013/0079827 A1 | 3/2013 | Neary et al. |
| 2013/0261680 A1 | 10/2013 | Baccelli et al. |
| 2013/0268011 A1 | 10/2013 | Rezach et al. |
| 2018/0036041 A1 | 2/2018 | Pham et al. |

FOREIGN PATENT DOCUMENTS

| | | |
|---|---|---|
| CN | 101249017 A | 8/2008 |
| CN | 102368967 A | 3/2012 |
| CN | 102458279 A | 5/2012 |
| DE | 9314297 U1 | 4/1994 |
| DE | 4329220 A1 | 3/1995 |
| DE | 29903342 U1 | 6/1999 |
| DE | 29810798 U1 | 10/1999 |
| DE | 19912364 A1 | 10/2000 |
| DE | 20207785 U1 | 9/2003 |
| EP | 0408489 B1 | 9/1994 |
| EP | 0674880 A1 | 10/1995 |
| EP | 0828459 A1 | 3/1998 |
| EP | 0837656 A1 | 4/1998 |
| EP | 0612507 B1 | 12/1998 |
| EP | 0683644 B1 | 6/2000 |
| EP | 1198205 A1 | 4/2002 |
| EP | 1210914 A1 | 6/2002 |
| EP | 0807420 B1 | 7/2002 |
| EP | 1248573 A1 | 10/2002 |
| EP | 1269929 A1 | 1/2003 |
| EP | 1316295 A2 | 6/2003 |
| EP | 1323391 A2 | 7/2003 |
| EP | 1637085 A2 | 3/2006 |
| EP | 1313403 B1 | 10/2006 |
| EP | 1741396 A1 | 1/2007 |
| EP | 1815812 A1 | 8/2007 |
| EP | 1665994 B1 | 6/2008 |
| EP | 1928358 A2 | 6/2008 |
| EP | 1961392 A1 | 8/2008 |
| EP | 2052690 A1 | 4/2009 |
| EP | 1294297 B1 | 8/2010 |
| ES | 2330132 T3 | 12/2009 |
| GB | 2414674 B | 8/2009 |
| GB | 2465156 A | 5/2010 |
| JP | 06-154258 | 6/1994 |
| JP | 08-112291 A | 5/1996 |
| JP | 08-206976 A | 8/1996 |
| JP | 2005-510286 | 4/2005 |
| JP | 2006-508748 A | 3/2006 |
| JP | 2006-154258 | 6/2006 |
| JP | 2006-525102 A | 11/2006 |
| JP | 2009-535114 A | 10/2009 |
| JP | 2012-523927 A | 10/2012 |
| JP | 2012-530550 A | 12/2012 |
| KR | 10-2008-0112851 A | 12/2008 |
| KR | 10-0896043 B1 | 5/2009 |
| KR | 10-2012-0013312 A | 2/2012 |
| KR | 10-2012-0039622 A | 4/2012 |
| WO | 94/17736 A1 | 8/1994 |
| WO | 96/32071 A1 | 10/1996 |
| WO | 97/02786 A1 | 1/1997 |
| WO | 98/08454 | 3/1998 |
| WO | 98/52482 A1 | 11/1998 |
| WO | 2000/015125 A1 | 3/2000 |
| WO | 00/21455 A1 | 4/2000 |
| WO | 01/06940 A1 | 2/2001 |
| WO | 01/52758 A1 | 7/2001 |
| WO | 02/00124 A1 | 1/2002 |
| WO | 02/17803 A2 | 3/2002 |
| WO | 02/76314 A1 | 10/2002 |
| WO | 2003/045261 A1 | 6/2003 |
| WO | 2004/052218 A1 | 6/2004 |
| WO | 2004/089245 A2 | 10/2004 |
| WO | 2004/098425 A2 | 11/2004 |
| WO | 2005/016161 A1 | 2/2005 |
| WO | 2006/088452 A2 | 8/2006 |
| WO | 2006/114437 A1 | 11/2006 |
| WO | 2006/116437 A2 | 11/2006 |
| WO | 2006/135555 A2 | 12/2006 |
| WO | 2007/038350 A2 | 4/2007 |
| WO | 2007/040824 A2 | 4/2007 |
| WO | 2007/045892 A1 | 4/2007 |
| WO | 2007/047711 A2 | 4/2007 |
| WO | 2007/127632 A2 | 11/2007 |
| WO | 2007/146032 A2 | 12/2007 |
| WO | 2008/027940 A2 | 3/2008 |
| WO | 2008/048953 A2 | 4/2008 |
| WO | 2008/069420 A1 | 6/2008 |
| WO | 2008/089096 A2 | 7/2008 |
| WO | 2008/146185 A1 | 12/2008 |
| WO | 2008/147663 A1 | 12/2008 |
| WO | 2009/001978 A1 | 12/2008 |
| WO | 2009/015100 A2 | 1/2009 |

(56) References Cited

FOREIGN PATENT DOCUMENTS

| WO | 2010/030906 A1 | 3/2010 |
| WO | 2010/028287 A3 | 6/2010 |
| WO | 2010/120989 A1 | 10/2010 |
| WO | 2010/148231 A1 | 12/2010 |
| WO | 2012/154772 A2 | 11/2012 |

OTHER PUBLICATIONS

International Patent Application No. PCT/US2006/037120: International Search Report dated Jul. 11, 2007, 4 pages.

International Patent Application No. PCT/US2006/047986: International Search Report dated May 2, 2007, 2 pages.

International Patent Application No. PCT/US2010/031178: International Search Report dated Jun. 22, 2010, 8 pages.

International Patent Application No. PCT/US2008/070670: International Preliminary Report )n Patentability dated Jul. 9, 2009, 6 pages.

International Patent Application No. PCT/US2008/070670: International Search Report dated Feb. 17, 2009, 5 pages.

International Patent Application No. PCT/US2009/056692: International Search Report and Written Opinion dated Dec. 3, 2009, 14 pages.

International Patent Application No. PCT/US2010/031178: Notification of Transmittal of The International Preliminary Report on Patentability dated Jun. 14, 2011,12pages.

International Patent Application No. PCT/US2010/039037: International Preliminary Report on Patentability dated Jul. 11, 2011.

International Patent Application No. PCT/US2010/039037: International Search Report dated Jan. 9, 2010, 5 pages.

International Preliminary Report on Patentability dated Dec. 4, 2011 in application PCT/US2009/058788, 7 pgs.

International Preliminary Report on Patentability dated May 3, 2011 in PCT application PCT/US2009/063056.

U.S. Provisional Application Filed on Apr. 15, 2009 by Nicholas Theodore et. al., entitled "Revision Connector for Spinal Constructs", U.S. Appl. No. 61/169,336.

U.S. Provisional Application Filed on Jun. 17, 2009 by Albert Montello et. al., entitled Top-Loading Polyaxial Construct Extender for Spinal Surgery, U.S. Appl. No. 61/187,902.

"Secure" Cambridge Dictionary accessed Feb. 27, 2021 https://dictionary.cambridge.org/us/dictionary/english/secure (Year: 2021).

* cited by examiner

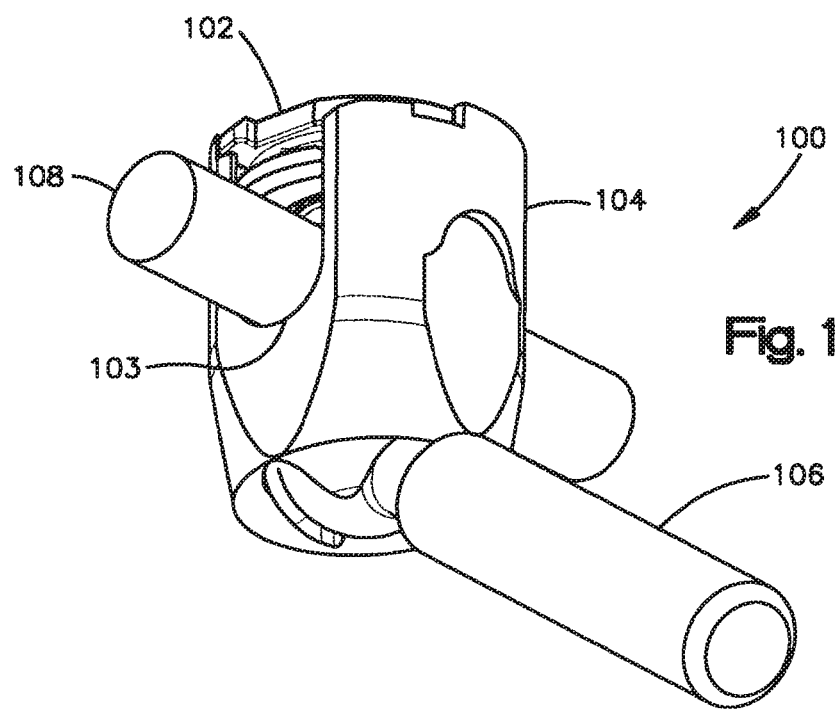
Fig. 1
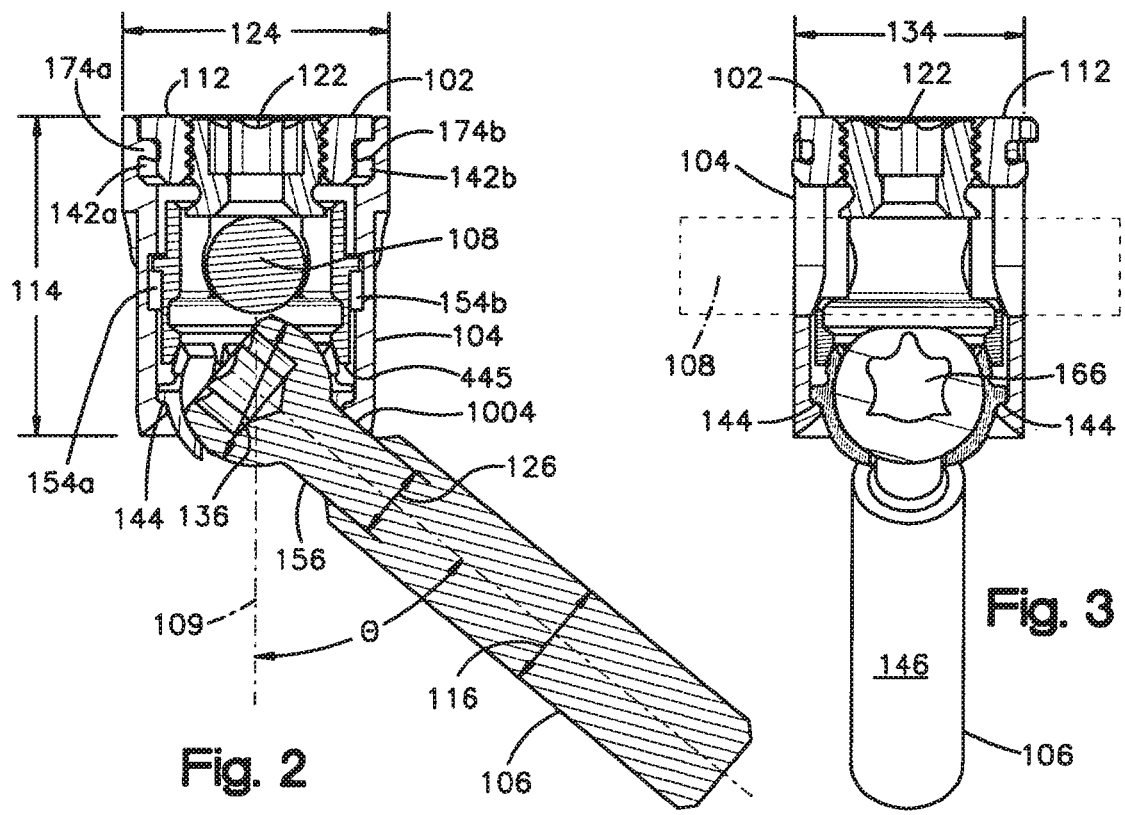
Fig. 2
Fig. 3

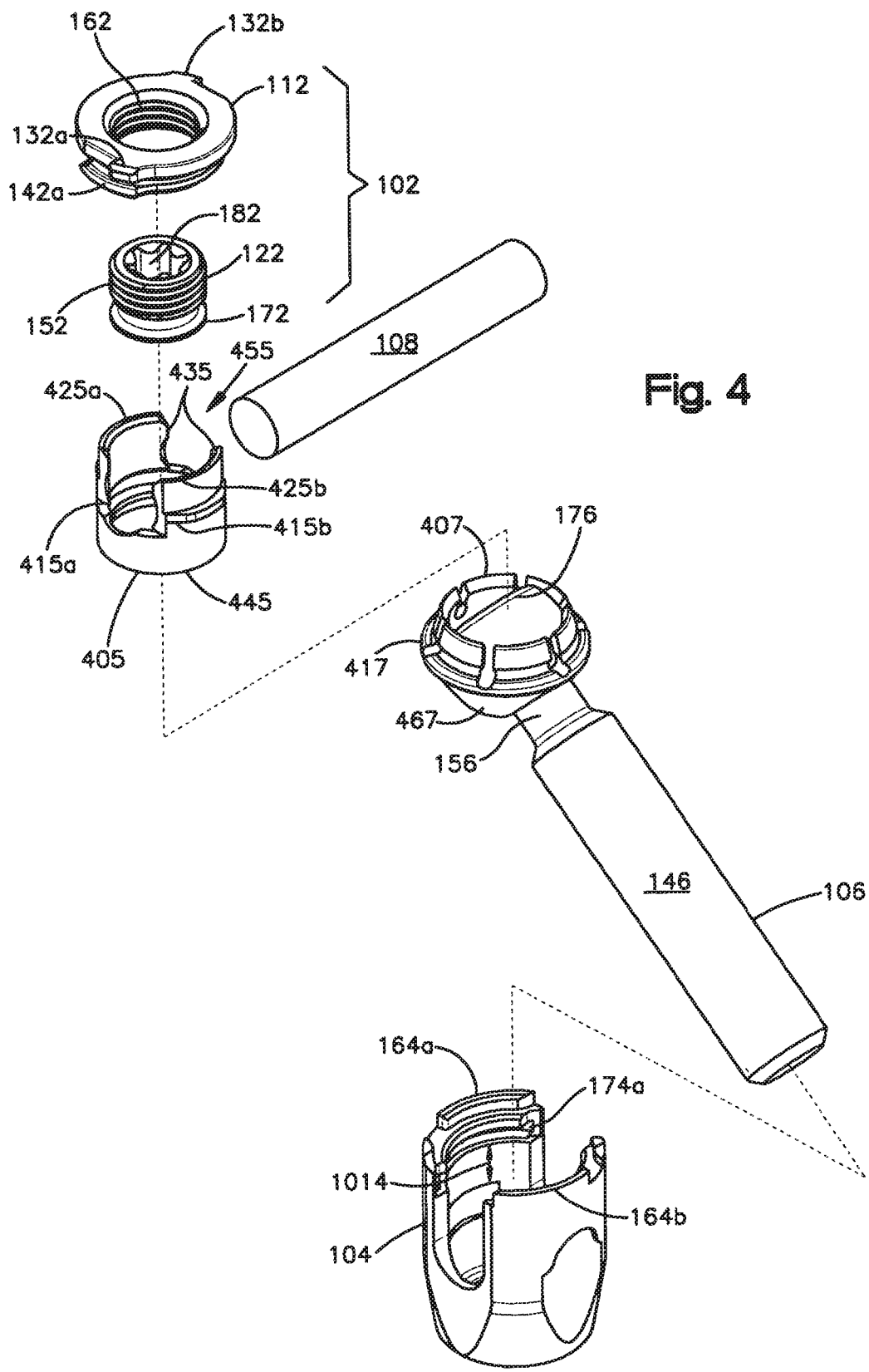

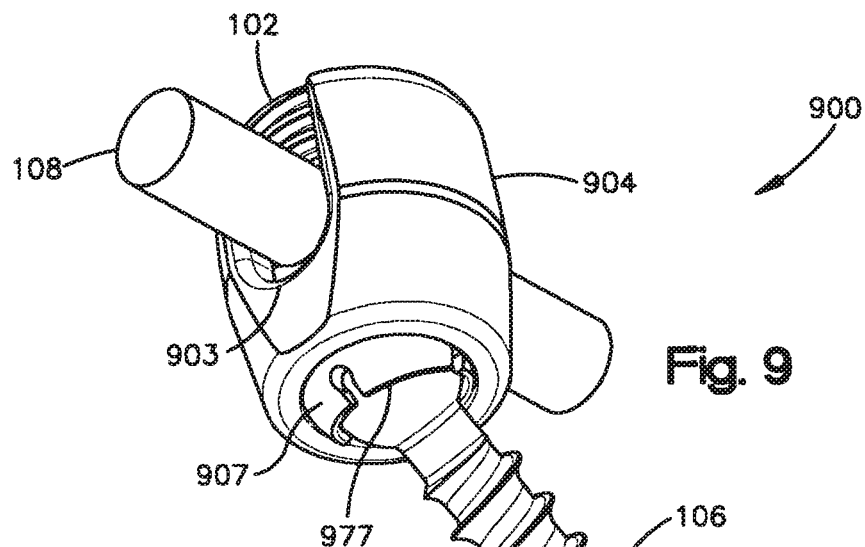
Fig. 9
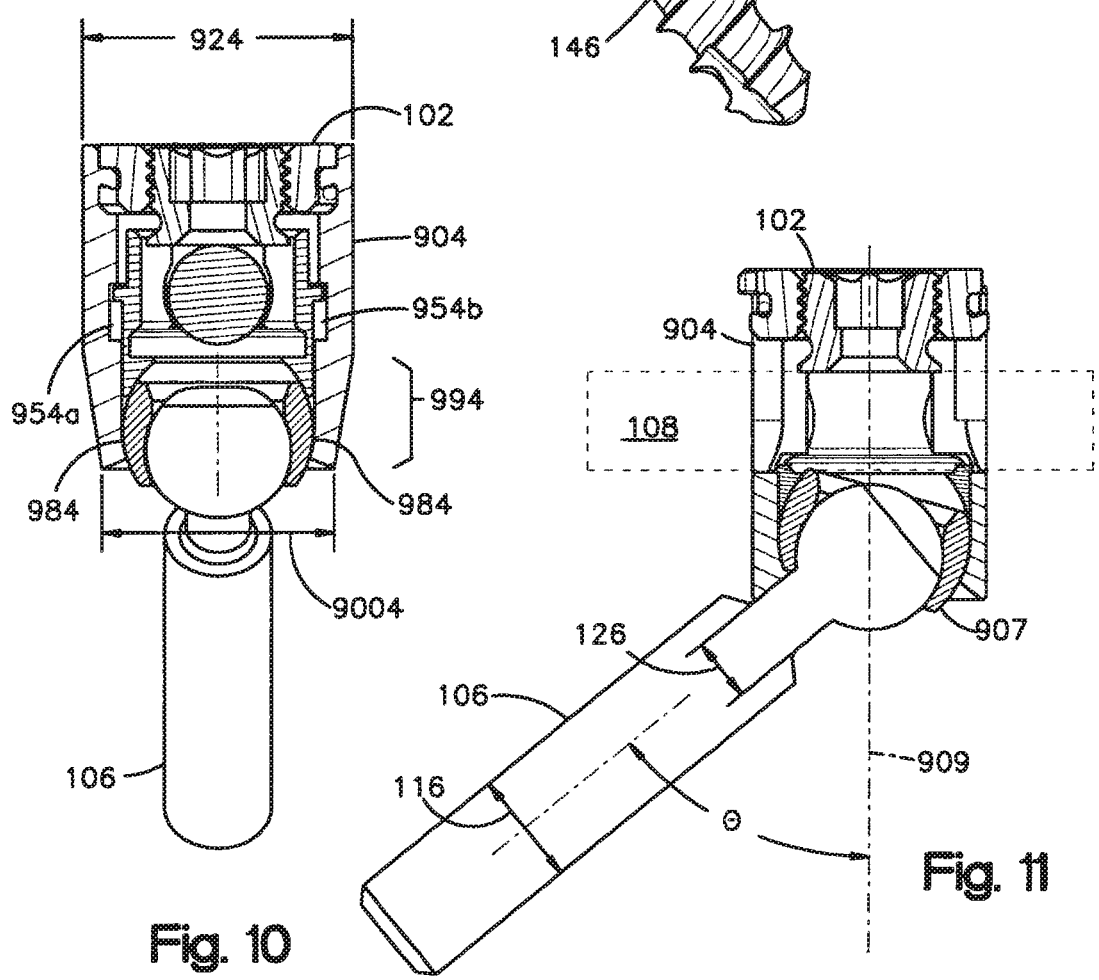
Fig. 10
Fig. 11

POLYAXIAL BONE ANCHORS WITH INCREASED ANGULATION

CROSS REFERENCE TO RELATED APPLICATIONS

This application is a continuation of U.S. patent application Ser. No. 15/803,088, filed Nov. 3, 2017, now allowed, which is a continuation of U.S. patent application Ser. No. 14/187,947, filed Feb. 24, 2014, now U.S. Pat. No. 9,848,918, issued Dec. 26, 2017, which is a continuation of U.S. patent application Ser. No. 13/688,600, filed Nov. 29, 2012, now U.S. Pat. No. 9,504,498, issued Nov. 29, 2016. U.S. patent application Ser. No. 13/688,600 is a continuation of U.S. patent application Ser. No. 13/329,755, filed Dec. 19, 2011, now U.S. Pat. No. 8,679,162, issued Mar. 25, 2014. U.S. patent application Ser. No. 13/329,755 is a continuation of U.S. patent application Ser. No. 11/603,428, filed Nov. 21, 2006, now U.S. Pat. No. 8,100,946, issued Jan. 24, 2012. U.S. Pat. No. 8,100,946, as well as each application listed in this paragraph, claims the benefit of U.S. Provisional Application No. 60/739,100, filed Nov. 21, 2005.

TECHNICAL FIELD

This invention relates to bone fixation devices and related methods of fixation. More particularly, this invention relates to polyaxial bone anchors, such as pedicle screws and hooks, having increased angulation for use in, for example, the posterior fixation of the spine.

BACKGROUND

Polyaxial bone anchors and methods of use in treating spinal disorders are known. Typical methods involve anchoring at least two screws or hooks into the vertebrae, and fixing the screws or hooks along a spinal rod to position or immobilize the vertebrae with respect to one another. The screws or hooks commonly have anchor heads with U-shaped channels in which the spinal rod is inserted and subsequently clamped by a fastener, such as, for example, a threaded nut, set screw or locking cap. These methods commonly involve multiple screws or hooks and multiple spinal rods. The spinal rod(s) may be shaped to maintain the vertebrae in a desired orientation so as to correct the spinal disorder at hand (e.g., to straighten a spine having abnormal curvature). Additionally or alternatively, the screws or hooks may be spaced along the rods(s) to compress or distract adjacent vertebrae.

Surgeons may encounter difficulty with spinal fixation and stabilization methods because of difficulty aligning the spinal rod(s) with the U-shaped channels in the anchor heads of the screws or hooks. For example, the anchor heads are often out of alignment with one another because of the curvature of the spine or the size and shape of each vertebrae. To facilitate easier insertion of the spinal rods into the U-shaped channels, and to provide additional flexibility in the positioning of the spinal rods and the screws and hooks, bone anchors have been developed where the anchor member (e.g., screw or hook) and anchor head can initially pivot or rotate with respect to each other. These bone anchors are sometimes referred to as polyaxial bone anchors and the pivot or rotation of the anchor member is referred to as angulation.

A disadvantage of many polyaxial bone anchors is the degree to which the anchor head and member can angulate. Typical polyaxial bone anchors have anchor members that can rotate up to about 30° from a central axis extending down through the anchor head. It may be advantageous to provide polyaxial bone anchors with increased angulation.

SUMMARY OF THE INVENTION

The invention is directed to polyaxial bone anchors and methods of use for attaching a rod, such as a support or spinal rod, to a bone, such as a vertebra. The bone anchor may include a hollow generally cylindrical housing or head (referred to hereinafter as an anchor head), an optional hollow generally cylindrical internal sleeve, an internal locking element, a pedicle screw for other type of anchor member, such as, for example, a hook or other similar structure), and preferably a locking cap with set screw (alternatively, other types of fasteners and fastening arrangements, such as, for example, a threaded nut or locking sleeve mounted on or over the top portion of the head, are also within the scope of the invention). The anchor head and internal sleeve may have a U-shaped channel for receiving a support/spinal rod (referred to hereinafter as a spinal rod or rod). The locking element preferably is sized and shaped to snap on to the head of the pedicle screw. And the locking cap and set screw may close the top opening of the U-shaped channel after a rod has been placed therein and, in combination with the locking element, lock or clamp the respective positions of the pedicle screw and rod.

The anchor head, the internal sleeve, and primarily the locking element have features that allow the locking element to rotate or pivot within the anchor head. This in turn allows the pedicle screw to rotate or pivot around and away from the central axis of the anchor head at large angles. The pedicle screw or hook may be locked with respect to the anchor head at these large angles. The angulation is preferably as much as about 50° in every direction from the central axis. This advantageously provides greater flexibility to the surgeon when aligning spinal rods with the anchor heads of implanted screws and hooks during surgery.

In one embodiment of the invention, the locking element, which can be described as a collet or collet-style bushing, has an upper portion with a plurality of resilient tabs to initially receive and hold the head of a pedicle screw. The internal sleeve has a bottom surface with a preferably corresponding inward taper to mate with the tapered shape of the exterior surface of the tabs on the collet to allow rotation and facilitate locking of the collet. The collet has at least one cutout of preferably about 50° on its lower side and the anchor head has a lower portion with a tapered inner surface that together make possible the large angulation of the pedicle screw mounted in the collet. The anchor head preferably also has an internal ledge for receiving a corresponding lip or projection on the collet to seat it within the head and allow it to rotate about the longitudinal axis of the bore of the anchor head so the cutout can be aligned in a desired direction for full angulation of the pedicle screw. The collet may have one or more cutouts and preferably has multiple cutouts. When the bone anchor is ready to be locked, the bottom interior surface of the internal sleeve presses down on the outside of the tabs of the collet so that the collet compresses around the screw head to lock the position of the screw.

In another embodiment of the invention, the locking element, which may be described as a spherical bushing, can rotate or swivel within the anchor head prior to locking. The anchor head has a lower portion with a spherically-cut inner surface that facilitates rotation of die spherical bushing about a point within the anchor head. The spherical bushing has a spherical exterior shape, a spherical interior shape, and preferably at least one slot that permits the bushing to compress the head of a pedicle screw or hook inserted into the interior of the spherical bushing. Preferably, the pedicle screw or hook has an arcuate or spherical upper portion (head) whose shape corresponds to the interior shape of the spherical bushing. The internal sleeve has a bottom interior surface with a spherical shape to mate with the exterior spherical shape of the top portion of the spherical bushing. The interior surface of the spherical bushing has a centerpoint that is preferably offset from the centerpoint of the exterior surface of the spherical bushing and hence the pedicle screw mounted within it. This offset provides additional angulation as follows: The pedicle screw angulates a certain amount before its shank engages an edge of die spherical bushing. The spherical bushing can then rotate with the pedicle screw to provide the additional amount of angulation, the sum of which provides the increased angulation. When the bone anchor is ready to be locked, the internal sleeve is pressed down on the spherical bushing's top surface, so that the bushing compresses around the screw head to lock the position of the screw.

BRIEF DESCRIPTION OF THE DRAWINGS

The detailed description will be better understood in conjunction with the accompanying drawings, in which like reference characters refer to like parts throughout, and in which:

FIGS. 1-3 are perspective, side cross-sectional, and front cross-sectional views, respectively, of a first embodiment of a polyaxial bone anchor;

FIG. 4 is an exploded view of the polyaxial bone anchor of FIGS. 1-3;

FIGS. 9-11 are perspective, side cross-sectional, and front cross-sectional views, respectively, of a second embodiment of a polyaxial bone anchor;

DETAILED DESCRIPTION OF THE INVENTION

Figure 5A:
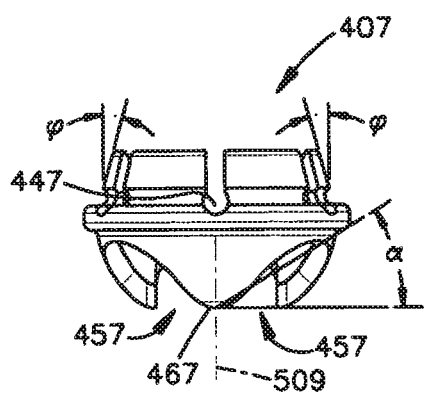
FIGS. 5A and 5B are elevational views of the locking element of the polyaxial bone anchor of FIGS. 1-4.
Figure 5B:
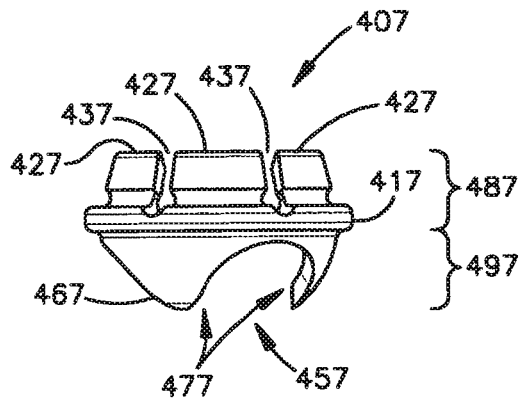

The invention can be used to treat various spinal disorders including, for example, degenerative instabilities and instabilities due to decompression, tumors, infections, and fractures.

Note that while the polyaxial bone anchor is described and illustrated herein with reference to certain preferred or exemplary embodiments, the invention should not be limited to those preferred or exemplary embodiments. Furthermore, the features described and illustrated herein can be used singularly or in combination with other features and embodiments.

FIGS. 1-3 show a first embodiment of a polyaxial bone anchor. Polyaxial bone anchor 100 includes a fastener 102, an anchor head 104, and an anchor member 106. Fastener 102 is a locking cap that includes a locking ring 112 and a set screw 112 and may be similar or identical to that described in International Patent Application PCT/US2006/015692, internationally filed Apr. 25, 2006, which is incorporated herein by reference in its entirety. Alternatively, fastener 102 may be any known fastener, and anchor head 104 may have any corresponding features required to permit attachment and operation of fastener 102 (e.g., threaded upper arms). Anchor head 104 is preferably cylindrically hollow having a generally longitudinal bore 1014 along longitudinal axis 109. Anchor head 104 also has a generally U-shaped opening 103 transverse to longitudinal bore 1014 for receiving a spinal rod 108 or other similar part. Longitudinal bore 1014 has a top opening 194 and a bottom opening 184. Anchor member 106, which may be a bone or pedicle screw, hook, or other similar structure (and will be referred to hereinafter as pedicle screw 106), extends out of bottom opening 184. Anchor member 106 may be coupled to anchor head 104 such that the head and screw can polyaxially rotate with respect to each other when in an unlocked position, but the angle of the longitudinal axis of anchor member 106 may be fixed with respect to the longitudinal axis of anchor head 104 in a locked position.

One or more polyaxial bone anchors 100 may be attached, for example, to the vertebrae via respective anchor members 106, and a spinal rod 108 or other similar part can be inserted into the U-shaped openings 103. The spinal rod may thereafter be locked with respect to anchor head 104. A system of bone anchors and rods could be used to correctly align the spine or treat other spinal disorders.

Representative dimensions of bone anchor 100 include an anchor head height 114 of about 11.5 mm, a width 124 of about 9.5 mm, and a length 134 of about 8.2 mm. Pedicle screw 106 has a shank diameter 116 of about 4 mm, a neck diameter 126 of about 2.75 mm, and head diameter 136 of about 5.4 mm. Alternatively, bone anchor 100 may be of other dimensions.

Advantageously, pedicle screw 106 can angularly rotate (before being locked or clamped in place) about central axis 109 by an angle θ of preferably about 50° in any direction (i.e., the angular rotation of the head of anchor member 106 in the anchor head forms a cone of preferably about 100°).

FIG. 4 shows an exploded view of the assembly of bone anchor 100, which includes locking ring 112 and set screw 122 of locking cap 102, a hollow generally cylindrically shaped internal sleeve 405, a spinal rod 108, an internal locking element 407, a pedicle screw 106 (shown mounted in locking element 407), and an anchor head 104. Bone anchor 100 is first assembled by snap-fitting locking element 407 over the head of pedicle screw 106.

As shown in FIGS. 5A and B, locking element 407 may be described as a collet or collet-styled bushing (referred to hereinafter as collet 407). Collet 407 is made of a resilient material that can be compressed around the head of pedicle screw 106 to retain pedicle screw 106 securely in place. Preferably the material of the collet is softer than the material of internal sleeve 405 and pedicle screw 106.

Figure 6:
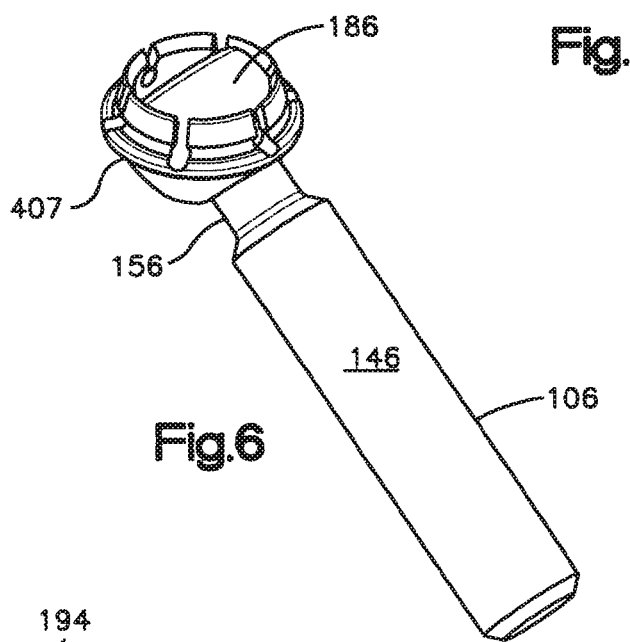
FIG. 6 is a perspective view of the locking element of FIGS. 1-4 with a pedicle screw mounted therein.

Preferably, the upper portion 487 of collet 407 provides the collet with most, it not all, of its screw head retention capabilities. Upper portion 487 has a plurality of resilient tabs 427. The exterior surface of tabs 427 preferably are tapered inward at an angle φ of preferably about 30°, although angles φ are alternatively possible and contemplated. Tabs 427 can deflect outward to allow the head 186 of pedicle screw 106 to be inserted within al space of the collet, as shown in FIG. 6. The internal space 477 of collet 407 is shaped to substantially match the shape of the pedicle screw head such that the collet has to be pressed over the screw head in a friction fit. Preferably, the head 186 of the pedicle screw and the internal space of the collet have at least a portion which is spherically shaped. Tabs 427 are separated by slots 437, which may also have a radius or circular shaped portion 447 as a stress relief and/or to provide better resiliency to tabs 427. The arrangement, shapes, and dimensions of the tabs/slots optionally may be different than shown.

Figure 7:
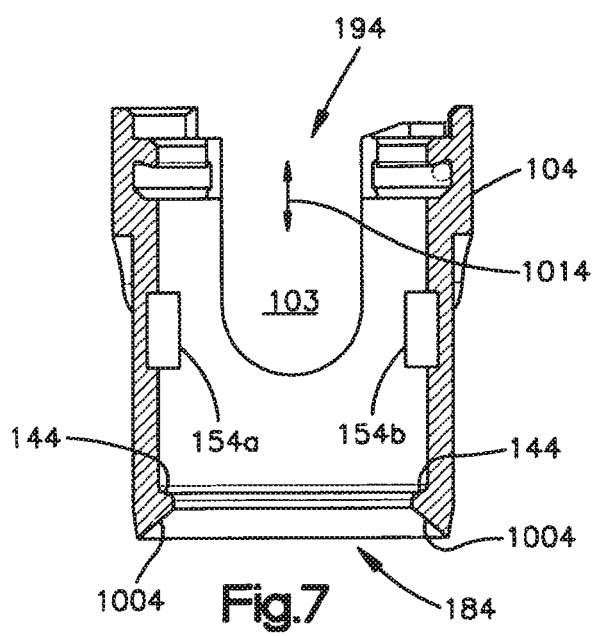
FIG. 7 is a side cross-sectional view of the anchor head of the polyaxial bone anchor of FIGS. 1-4.

The collet/screw assembly is then inserted screw-shank first through the top opening 194 in anchor head 104 until circumferential lip 417 of collet 407 is seated against circumferential internal ledge 144 of anchor head 104 (see FIGS. 2, 3, and 7). Screw shank 146 of pedicle screw 106 now protrudes through the bottom opening 184 of anchor head 104 as shown in FIGS. 1-3. The diameter of collet 407 at lip 417 preferably is such that it can pass through the top opening 194 of anchor head 104, but cannot pass through the bottom opening 184 and more particularly internal ledge 144 of anchor head 104.

The lower portion 497 of collet 407 has one or more cutouts 457 of angle α, which is measured from the bottom of collet 407 at central axis 509 (which coincides with central axis 109 when collet 407 is seated in anchor head 104) to the top of the cutout, as shown in FIG. 5A. Preferably angle α is about 50°. (other angles α are alternatively possible). The embodiment of collet 407 shown in FIG. 5A has three 50° cutouts 457. Embodiments with two, four, or more cutouts are possible. Cutouts 457 make possible the larger angulation between the anchor head and pedicle screw where cutouts are located. Collet 407 may rotate or swivel about axis 109 within anchor head 104, prior to the locking of the pedicle screw, to position a cutout in a preferred direction in which to provide full (i.e., maximum) angulation. For example, if a cutout is not aligned as desired, pedicle screw 106 will press against a prong 467 as a surgeon angulates anchor head 104 in a desired direction. This pressing preferably causes collet 407 to rotate within anchor head 104 until cutout 457 is aligned in the desired direction.

The number of cutouts represents a tradeoff between versatility and screw retention capability. That is, a collet with more cutouts has more positions at which to provide full angulation and is thus more easily aligned (i.e., such a collet does not need to be rotated as much to be aligned as a collet with fewer cutouts). However, retention capability (e.g., friction and gripping strength) is in part a function of the amount of surface area in contact with the pedicle screw head. If more area is in contact with the screw head (e.g., because the collet has fewer cutouts), more friction to provisionally hold the pedicle screw in place before locking and more gripping strength to lock the screw in place is available. If more cutouts are provided, less surface area may contact the pedicle screw head, and less friction and gripping strength may be provided.

Also facilitating the angulation of pedicle screw 106 is a preferably tapered lower portion inner surface 1004 of anchor head 104, as shown in FIG. 7. Pedicle screw 106 will angulate until the neck 156 of the screw butts against inner surface 1004, as best shown in FIG. 2.

Internal sleeve 405, which may be optional in some embodiments, is next inserted downward into anchor head 104. Internal sleeve 405 preferably provides a U-shaped channel 455 transverse to a longitudinal bore in sleeve 405. Internal sleeve 405 preferably has a pair of retention tabs 415a,b on its outer surface that snap into respective slots 154a,b on opposite walls of anchor head 104 (best seen in FIG. 2). This aligns the U-shaped channels of anchor head 104 and sleeve 405. Slots 154a,b of anchor head 104 allow sleeve 405 to move up and down from an unlocked screw position to a locked screw position, respectively, on top of collet 407, while retaining the sleeve within the anchor head. Tabs 415a,b may also keep the U-shaped channel in sleeve 405 aligned with the U-shaped opening in the anchor head. Alternatively, other means of keeping U-shaped channel 455 in sleeve 405 aligned with U-shaped opening 103 in anchor head 104 may used, such as, for example, protruding tabs along the boundary of U-shaped channel 455 that project or snap into space provided by the U-shaped opening in anchor head 104.

With fastener 102 removed from the assembly of the anchor head, internal sleeve, collet, and pedicle screw, the pedicle screw may be attached to a bone. The head of pedicle screw 106 preferably has a recess 166 (as shown in FIG. 3) or slot 166 (as shown in FIG. 4) keyed to receive a hex wrench, torque wrench, or other known driver (through the aforementioned assembly) to implant the pedicle screw by rotating into, for example, a vertebra.

Anchor head 104 may now be aligned to receive a rod 108. Rod 108 is preferably snapped into internal sleeve 405. The distance between upright arms 425a,b of sleeve 405 across the narrowest widths 435 of the U-shaped channel is preferably slightly less than the diameter of rod 108. For example, if rod 108 has a diameter of about 3.5 mm, the aforementioned distance would preferably be about 3.26 mm. In this manner, the sleeve may provisionally retain the spinal rod but still permit the rod to slide in the U-shaped channel or be removed. Alternatively or additionally, sleeve 405, with or without the spinal rod, can be pushed down in the anchor head (e.g., be pushing down on the spinal rod in the U-shaped channel) so that the under surface of sleeve 405 interacts with tabs 427 on collet 407 to provisionally lock the pedicle screw with respect to the anchor head. In this manner, the spinal rod is still permitted to slide within and/or be removed from the sleeve.

With the spinal rod in the U-shaped channel (with or without the head of the screw or hook being locked in the anchor head), the locking cap 102 may be placed on anchor head 104, closing the U-shaped channel. In this embodiment, locking cap 102 is first positioned on top of anchor head 104 and pressed downward until it snaps into position. The locking cap is then rotated until oppositely-positioned projections 132a,b on locking ring 112 contact corresponding structures 164a,b, respectively, on anchor head 104. As this occurs, a pair of oppositely-positioned, preferably dovetailed, lateral flanges 142a,b on locking ring 112 slide within corresponding, preferably dovetailed, grooves 174a,b, respectively, on anchor head 104. Preferably, locking ring 112 and the upper surfaces of anchor head 104 do not engage each other with screw threads, although screw threads may be used, as well as different locking caps.

At this stage, rod 108 can still be positioned (e.g., moved) relative to anchor head 104 and pedicle screw 106. Upon satisfactory positioning of the rod and pedicle screw, set screw 122 is driven downward to lock the rod and anchor head in place. Set screw 122 has external threads 152 that mate with internal threads 162 of locking ring 112. Preferably, the set screw is screwed into the locking ring before the locking cap is inserted into the anchor head, and preferably the set screw cannot be screwed out of the locking ring because of a flared portion 172 at the bottom of the set screw. Set screw 122 preferably also has a star socket 182. Alternatively, set screw 122 can have other types of sockets or recesses keyed to other known drivers or tools. A single instrument/tool may be used with locking cap 102 to drive in a single action both locking ring 112 and set screw 122 simultaneously to lock locking cap 102 in place on the anchor head and then to continue driving set screw 122 alone until rod 108 and pedicle screw 106 are clamped in place.

Figure 8:
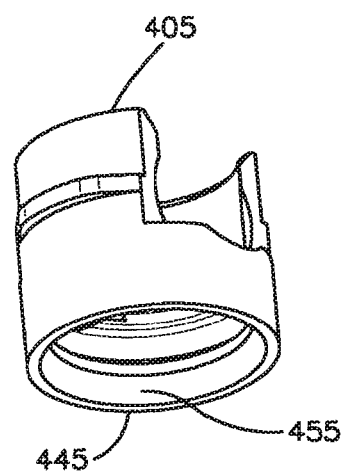
FIG. 8 is a perspective view showing the bottom of the internal sleeve of the polyaxial bone anchor of FIGS. 1-4.

As set screw 122 contacts rod 108, rod 108 pushes down on internal sleeve 405. As the downward rotation of set screw 122 continues, if internal sleeve 405 is in the upper position in anchor head 104, internal sleeve 405 moves downward within anchor head 104 compressing and ultimately crush-locking collet 407 around the head of pedicle screw 106, locking pedicle screw 106 with respect to anchor head 104. As shown in FIG. 8, internal sleeve has a bottom interior surface 455 preferably tapered inward by preferably about 30° so as to mate with the tapered tabs 427 of collet 407. Set screw 122 may be driven downward until (1) retention tabs 415a,b of sleeve 405 contact the bottom of slots 154a,b on anchor head 104, (2) the bottom edge 445 of sleeve 405 and lip 417 of collet 407 are clamped against internal ledge 144 of anchor head 104, and/or (3) tabs 427 are compressed against the head of the pedicle screw such that the sleeve can no longer travel down the bore of the anchor head. The set screw will push the spinal rod into the bottom of the U-shaped channel in sleeve 405 in order to move the sleeve down the bore of the anchor head. Once the sleeve can no longer move the sleeve down the bore of the anchor head, the set screw will apply pressure to the spinal rod so that it becomes locked in a final position in the sleeve (and in anchor head 104) so that the rod cannot slide and/or be removed from the anchor head.

Alternatively, other fasteners or caps may be used.

Collet 407 may be advantageously used with other types of anchor heads, internal sleeves, fasteners, and pedicle screws than those shown herein. For example, collet 407 may be used with similar corresponding bone anchor elements disclosed in the previously cited U.S. Provisional Patent Application No. 60/674,877, filed Apr. 25, 2005, incorporated herein by reference in its entirety.

FIGS. 9-11 show a second embodiment of a polyaxial bone anchor. Polyaxial bone anchor 900 includes fastener 102, an anchor head 904, and an anchor member 106. Anchor head 904 is substantially similar to anchor head 104 and is cylindrically hollow having a longitudinal bore 9014, top opening 9194, bottom opening 9184, and a generally U-shaped opening 903 transverse to the longitudinal bore for receiving spinal rod 108 or other similar part. Unlike anchor head 104, however, side lower portion 994 of anchor head 904 may have an inward taper. In one embodiment, side lower portion 994 may taper inward by about 0.65 mm on each side such that, for example, an upper width 924 of about 9.5 mm results in a lower width 9004 of about 8.2 mm. Bone anchor 100 may have the taper illustrated in this second embodiment and alternatively, bone anchor 900 may not have a taper as illustrated. Other representative dimensions of bone anchor 900 may be identical to those of bone anchor 100, and bone anchor 900 alternatively may be of other dimensions.

As with bone anchor 100, anchor member 106 (which will again be referred to hereinafter as pedicle screw 106) may be associated with or coupled to anchor head 904 such that the head and screw can polyaxially rotate with respect to each other. In particular, pedicle screw 106 can advantageously polyaxially rotate (before being locking or clamped in place) about central axis 909 of anchor head 904 by an angle θ of preferably about 50° in any direction (i.e., the angular rotation of the head of pedicle screw 106 in anchor head 904 forms a tone of preferably about 100°).

Figure 12:
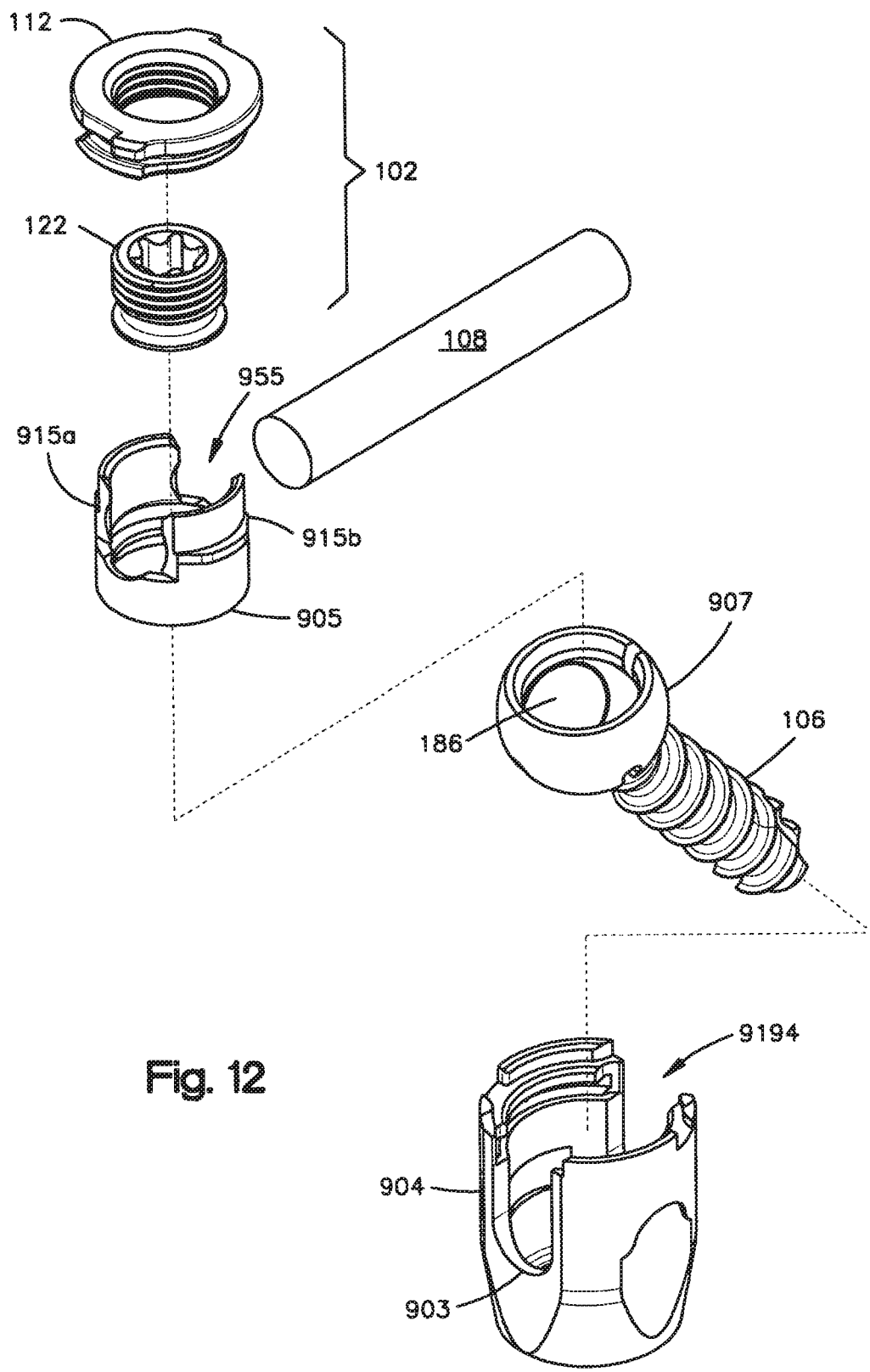
FIG. 12 is an exploded view of the polyaxial bone anchor of FIGS. 9-11.

FIG. 12 shows an exploded view of the assembly of bone anchor 900, which includes locking ring 112 and set screw 122 of locking cap 102, a hollow internal sleeve 905, spinal rod 108, an internal locking element 907, pedicle screw 106 (shown mounted in locking element 907), and anchor head 904. The assembly of bone anchor 900 is substantially, if not completely, identical to bone anchor 100. Lucking element 907 is first snap-fitted onto the head 186 of pedicle screw 106. The locking element/screw assembly is then inserted screw-shank first through the top opening 9194 of anchor head 904 until the lower exterior surface 977 of locking element 907 rests against corresponding spherical inner surface 984 on the lower portion of anchor head 904. This causes screw shank 146 of pedicle screw 106 to protrude through the bottom opening 9184 of anchor head 904. Internal sleeve 905 may be inserted through top opening 9194 so that the sleeve is retained in anchor head 904.

As shown in FIGS. 12-15, locking element 907 may be described as a spherical bushing (referred to hereinafter as bushing 907). Bushing 907 is made of a resilient material that can be compressed around the head of pedicle screw 106 to retain pedicle screw 106 securely in place. Preferably the material of the bushing is softer than the material of internal sleeve 905 and pedicle screw 106. Internal space 917 of bushing 907 is shaped to substantially match the shape of the pedicle screw head such that the bushing has to be pressed over the screw head. Preferably, internal space 917 of the bushing has an arcuate or spherical shape to correspond to the preferably spherical or arcuate shape of the head of the pedicle screw. The exterior surface 987 of bushing 907 preferably has an arcuate or spherical shape. The inner surface 984 of lower portion 994 of anchor head 904 preferably has a corresponding arcuate or spherical shape so that bushing 907 can rotate or swivel in anchor head 904 about a point inside the anchor head and/or within the bore of the spherical bushing.

Figure 14:
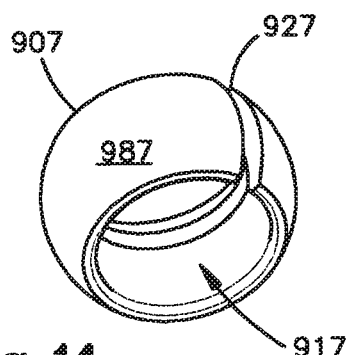
FIGS. 14 and 15 are perspective views of two embodiments, respectively, of the locking element of the polyaxial bone anchor of FIGS. 9-12.
Figure 15:
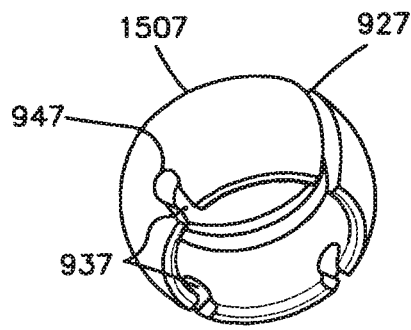
Figure 16:
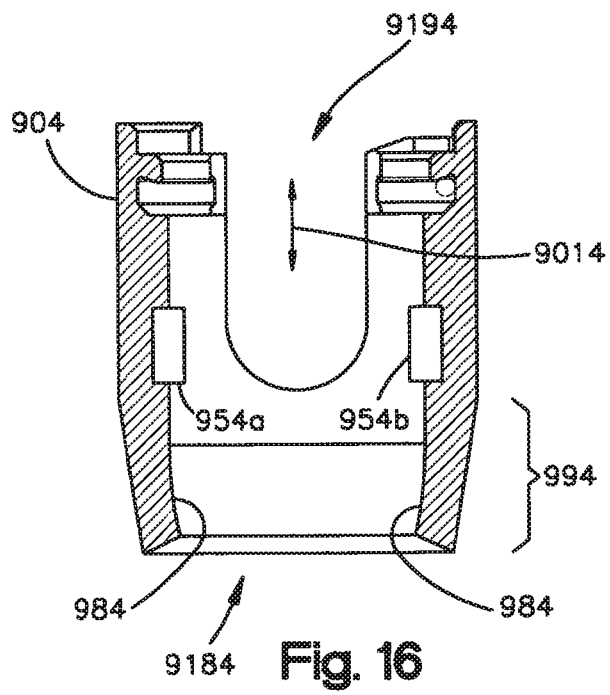
FIG. 16 is a side cross-sectional view of the anchor head of the polyaxial bone anchor of FIGS. 9-12.

Bushing 907 has a slot 927 to provide resiliency. Slot 927 may extend completely through from the exterior the side of bushing 907 to the interior side of the bushing and from the top end of the bushing, to the bottom end of the bushing as shown in FIG. 14. Another embodiment of a spherical bushing according to the invention is shown in FIG. 15, Bushing 1507 has additional slots 937 that do not extend completely from the top end of the bushing to the bottom end of bushing 1507. Slots 937 may also have a radius or circular shaped portion 947 as a stress relief and/or to provide better resiliency. The arrangement, shapes, and dimensions of the slots of bushings 907/1507 alternatively in be different than shown. For example, although slots 937 are shown as extending from the lower or bottom end of bushing 1507, some or all of slots 937 alternatively can extend from the top end of bushing 1507.

Figure 13:
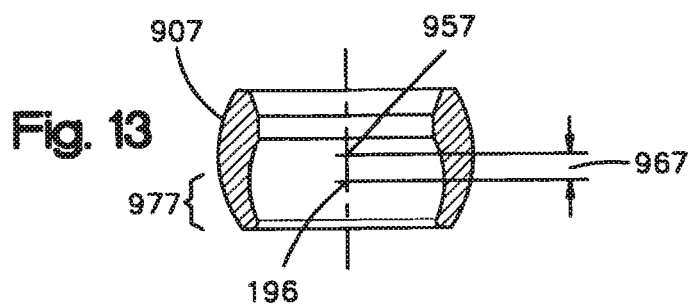
FIG. 13 is a cross-sectional view of the locking element of the polyaxial bone anchor of FIGS. 9-12.

Bushing 907 (and bushing 1507, referred to collectively hereinafter as bushing 907) can rotate or swivel about a point in the interior of the anchor head and/or bushing within anchor head 904 prior to locking. Inner surface 984 of anchor head 904 facilitates the rotation of bushing 907. As shown in FIG. 13, the inner surface of bushing 907 has a spherical centerpoint 957 that is preferably offset from the spherical centerpoint 196 of the exterior surface of bushing 907. This offset 967 is preferably about 0.6 mm (alternatively, offset 967 can be of other dimensions). In use, the pedicle screw may first angulate a certain amount until its shank 146 engages a lower edge 977 of bushing 907. At that point, bushing 907 can rotate with the pedicle screw to provide an additional amount of angulation, the sum of which provides the total angulation of the screw within the anchor head. The angulation of the screw within the bushing is preferably up to about 20° to about 30° of movement and the angulation of the bushing within the anchor head is preferably up to about 20° to about 30° of movement.

Alternatively, the centerpoints of bushing 907 and the pedicle screw head can be the same, which may maximize the retention capability of bushing 907 with respect to the screw head.

As with bone anchor 100, internal sleeve 905, which may be optional, is next inserted downward into anchor head 904. Internal sleeve 905 is positioned on top of bushing 907 and its insertion into and movement within anchor head 904 is substantially identical to that of internal sleeve 405 and anchor head 104. That is, internal sleeve 905 has a pair of retention tabs 915a,b on its outer surface that snap into respective slots 954a,b on opposite walls of anchor head 904. This insertion aliens the U-shaped channels of anchor head 904 and sleeve 905. Slots 954a,b of anchor head 904 allow sleeve 905 to move up and down from an unlocked screw position to a locked screw position, respectively. The sleeve may have the provisional locking features as described for bone anchor 100. Alternatively, other means of keeping U-shaped channel 955 of sleeve 905 aligned with U-shaped opening 903 in anchor head 904 may used, such as, for example, protruding tabs along the boundary of U-shaped channel 955 that project or snap into space provided by the U-shaped opening in anchor head 904.

With fastener 102 removed, the pedicle screw may be implanted in a bone, such as, for example, a vertebra, and anchor head 904 can thereafter be aligned to receive a spinal rod 108, which is snapped into internal sleeve 905 in a substantially, if not completely, identical manner as the corresponding parts of bone anchor 100.

Figure 17:
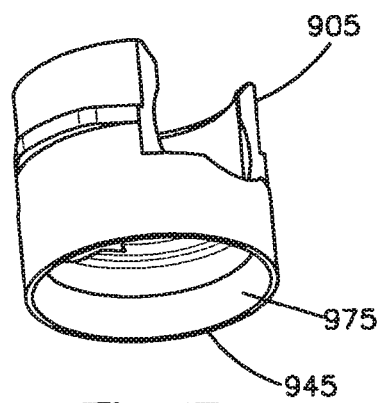
FIG. 17 is a perspective view showing the bottom of the internal sleeve of the polyaxial bone anchor of FIGS. 9-12.

Locking cap 102 is next placed on author head 904 and tightened to lock the rod and screw positions in a manner identical to that described above with respect to bone anchor 100. In particular, as set screw 122 contacts rod 108, rod 108 pushes down on internal sleeve 905. This causes internal sleeve 905 to move downward, compression locking bushing 907 against the head of pedicle screw 106. As shown in FIG. 17, internal sleeve 905 has a bottom surface 975 with a preferably corresponding arcuate or spherical shape that mates with the top portion of bushing 907. As with bone anchor 100, set screw 122 may be driven downward until retention tabs 915a,b of sleeve 905 contact the bottom of slots 954a,b on anchor head 904, until the bottom edge 945 of sleeve 905 raid bushing 907 are clamped against surface 984 of anchor head 904, or until sleeve 905 contacts bushing 907 so that further movement of sleeve 905 is not possible. Alternatively, other fasteners or caps may be used.

As with collet 407, bushing 907 may be advantageously used with other types of anchor heads, internal sleeves, fasteners, and pedicle screws than those shown herein. Bushing 907 may be used with similar corresponding bone anchor elements disclosed in the previously cited International Patent Application PCT/US2000/015692, internationally filed Apr. 25, 2006, incorporated herein by reference in its entirety. Bushing 907 provides an additional degree of freedom as compared to collet 407. Bushing 907 not only will rotate about the longitudinal axis extending through the bore of the anchor head, but will rotate about an axis extending transverse to the longitudinal axis.

The present invention has been described in connection with the preferred embodiments. These embodiments, however, are merely for example and the invention is not restricted thereto. It will be understood by those skilled in the art that other variations and modifications can easily be made within the scope of the invention as defined by the appended claims, thus it is only intended that the present invention be limited by the following claims.

What is claimed:

1. A polyaxial bone anchor configured to attach a rod to a bone, comprising:
   an anchor head defining a central axis and a longitudinal bore extending along the central axis, the longitudinal bore having a top opening and a bottom opening, the anchor head further defining a generally U-shaped channel transverse to the longitudinal bore and configured to receive the rod;
   a bushing configured to be retained within the anchor head, the bushing defining a first centerpoint and a second centerpoint offset from the first centerpoint; and
   an anchor member having a first portion that is configured to be retained by the bushing, and a second portion that extends through the bottom opening of the anchor head when the first portion is retained by the bushing,
   wherein the anchor member is configured to angulate with respect to the bushing about the first centerpoint until the second portion of the anchor member abuts the bushing so as to define a first range of angulation with respect to the central axis, and the bushing and the anchor member are configured to angulate together about the second centerpoint until the second portion of the anchor member abuts the anchor head so as to define a second range of angulation with respect to the central axis, wherein the second range of angulation is up to 30 degrees, and a sum of the first and second ranges of angulation is up to 50 degrees.

2. The polyaxial bone anchor of claim 1, wherein the bushing is compressively fit about the head of the anchor member, the bushing is made of a resilient material, and the bushing alone retains the first portion of the anchor member securely in place with respect to the bushing.

3. The polyaxial bone anchor of claim 2, wherein the bushing defines an inner surface and an outer surface, the inner surface defines the first centerpoint, and the outer surface defines the second centerpoint.

4. The polyaxial bone anchor of claim 3, wherein one or more of the inner and outer surfaces of the bushing is spherical.

5. The polyaxial bone anchor of claim 4, wherein:
   the outer surface of the bushing is spherical; and
   the anchor head has a lower portion that defines the bottom opening, the lower portion further defining a spherical inner surface that corresponds to the outer surface of the bushing.

6. The polyaxial bone anchor of claim 5, wherein the lower portion of the anchor head defines an outer surface that tapers toward the bottom opening.

7. The polyaxial bone anchor of claim 6, wherein the bushing defines a top surface and a bottom surface spaced from one another, and at least a portion of the bottom surface of the bushing extends outward from the bottom opening of the anchor head throughout an entirety of the second range of angulation.

8. The polyaxial bone anchor of claim 7, further comprising a sleeve retained within the anchor head, the sleeve having a top surface and a bottom surface spaced from the top surface of the sleeve, the bottom surface of the sleeve configured to abut the top surface of the bushing, the sleeve defining a second U-shaped channel capable of being aligned with the U-shaped channel of the anchor head, the second U-shaped channel extending transverse to the longitudinal bore, the second U-shaped channel configured to receive the rod therein.

9. The polyaxial bone anchor of claim 8, further comprising a fastener removably mountable to the anchor head to lock the rod in the U-shaped channel and the second U-shaped channel and press the sleeve against the bushing to compress the bushing against the first portion of the anchor member in a manner fixing a relative position between the anchor head and the anchor member.

10. The polyaxial bone anchor of claim 1, wherein the sum of the first and second ranges of angulation defines a total range of angulation of the anchor member about the central axis, and the total range of angulation forms a cone of 100 degrees.

11. The polyaxial bone anchor of claim 1, wherein the first portion of the anchor member is configured to angulate with respect to the bushing about the first centerpoint, and the bushing comprises a material that is resilient and is softer than a material of the first portion of the anchor member.

12. The polyaxial bone anchor of claim 1, wherein the bushing and the anchor member are configured to angulate together about the second centerpoint so as to define the second range of angulation after the anchor member has angulated with respect to the bushing about the first centerpoint and the second portion of the anchor member has abutted the bushing so as to define the first range of angulation.

13. A bone fixation system, comprising:
a spinal rod; and
a first polyaxial bone anchor configured to be anchored to a first vertebra and a second polyaxial bone anchor configured to be anchored to a second vertebra, wherein each of the first and second polyaxial bone anchors is configured to be coupled to the spinal rod so as to maintain a relative position between the first and second vertebra, wherein each of the first and second polyaxial bone anchors comprises:
an anchor head defining a central axis and a longitudinal bore extending along the central axis, the longitudinal bore having a top opening and a bottom opening, the anchor head further defining a generally U-shaped channel transverse to the longitudinal bore and configured to receive the spinal rod;
a bushing configured to be retained within the anchor head, the bushing defining a first centerpoint and a second centerpoint offset from the first centerpoint; and
an anchor member having a first portion that is configured to be retained by the bushing, and a second portion that is configured to extend through the bottom opening of the anchor head and into the respective first or second vertebra,
wherein the anchor member is configured to angulate with respect to the bushing about the first centerpoint so as to define a first range of angulation with respect to the central axis, and the bushing and the anchor member are configured to angulate together about the second centerpoint until the second portion of the anchor member abuts the anchor head so as to define a second range of angulation with respect to the central axis, wherein a sum of the first and second ranges of angulation is up to 50 degrees.

14. The bone fixation system of claim 13, wherein the first range of angulation is up to 30 degrees.

15. The bone fixation system of claim 13, wherein the second range of angulation is up to 30 degrees.

16. The bone fixation system of claim 13, wherein at least one of the bushings has an inner spherical surface that defines the first centerpoint and an outer spherical surface that defines the second centerpoint.

17. The bone fixation system of claim 16, wherein the at least one of the bushings defines a top surface and a bottom surface, and the second centerpoint of the at least one of the bushings is located between the first centerpoint and the bottom surface of the at least one of the bushings.

18. The bone fixation system of claim 17, wherein at least a portion of the at least one of the bushings extends outward from the bottom opening of the respective anchor head throughout an entirety of the respective second range of angulation.

19. The bone fixation system of claim 16, wherein the first and second centerpoints are offset by 0.6 mm.

20. The bone fixation system of claim 13, wherein each anchor head comprises a first material and each bushing comprises a second material that is softer than the first material, and the second material is a resilient material configured to allow each bushing to be compressed around the first portion of the respective anchor member to retain the respective anchor member in position relative to the respective bushing.

21. The bone fixation system of claim 13, wherein each of the first and second polyaxial bone anchors includes a fastener removably mountable to the respective anchor head to lock the rod in the respective U-shaped channel and compress the respective bushing against the first portion of the respective anchor member in a manner fixing a relative position between the spinal rod and the respective anchor member.

22. The bone fixation system of claim 13, wherein the bushing alone retains the first portion of the anchor member securely in place with respect to the bushing, and the bushing is made of a resilient material and is compressed around the first portion of the anchor member.

* * * * *